United States Patent
Herriges et al.

(10) Patent No.: US 12,082,783 B2
(45) Date of Patent: Sep. 10, 2024

(54) ENDOSCOPIC DEVICES AND RELATED METHODS

(71) Applicant: CooperSurgical, Inc., Trumbull, CT (US)

(72) Inventors: Catherine M. Herriges, Shelton, CT (US); Xiao Wu, Hamden, CT (US); Richard I. Farrington, Waterbury, CT (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 16/809,665

(22) Filed: Mar. 5, 2020

(65) Prior Publication Data

US 2020/0305699 A1    Oct. 1, 2020

Related U.S. Application Data

(60) Provisional application No. 62/825,962, filed on Mar. 29, 2019.

(51) Int. Cl.
*A61B 1/05*    (2006.01)
*A61B 1/00*    (2006.01)
(Continued)

(52) U.S. Cl.
CPC ............ *A61B 1/05* (2013.01); *A61B 1/00052* (2013.01); *A61B 1/00087* (2013.01); (Continued)

(58) Field of Classification Search
CPC ..... A61B 1/05; A61B 1/0008; A61B 1/00087; A61B 1/00089; A61B 1/00096;
(Continued)

(56) References Cited

U.S. PATENT DOCUMENTS

| | | | |
|---|---|---|---|
| 5,630,782 A | * | 5/1997 | Adair ................... A61B 1/12 600/156 |
| 6,679,882 B1 | | 1/2004 | Kornerup |

(Continued)

FOREIGN PATENT DOCUMENTS

| | | |
|---|---|---|
| CN | 203829018 | 9/2014 |
| DK | 199900414 | 3/2001 |

(Continued)

OTHER PUBLICATIONS

The International Search Report and Written Opinion of the International Searching Authority for International Application No. PCT/US2020/021133 dated Jul. 10, 2020.

(Continued)

*Primary Examiner* — Ryan N Henderson
*Assistant Examiner* — Pamela F Wu
(74) *Attorney, Agent, or Firm* — Fish & Richardson P.C.

(57) ABSTRACT

Endoscopic devices are disclosed for viewing and/or performing a surgery on a patient's organ, such as a uterus. In an embodiment, the endoscopic deice includes a housing, a cannula, an imaging system, and a flexible printed circuit (FPC). The cannula is configured for insertion through a cervix into a uterus. The cannula has a lumen that extends from a proximal end of the cannula to a distal end of the cannula. The proximal end of the cannula is secured within the housing. The imaging system is located at a distal end of the cannula and includes a camera and one or more light-emitting diodes (LEDs). The FPC extends within the lumen of the cannula and electrically connects the camera and the LEDs to electrical components located in the housing. The lumen is configured to provide a passage for a working tool.

27 Claims, 17 Drawing Sheets

(51) Int. Cl.
*A61B 1/018* (2006.01)
*A61B 1/06* (2006.01)
*A61B 10/04* (2006.01)

(52) U.S. Cl.
CPC ...... *A61B 1/00114* (2013.01); *A61B 1/00124* (2013.01); *A61B 1/00128* (2013.01); *A61B 1/018* (2013.01); *A61B 1/0676* (2013.01); *A61B 1/0684* (2013.01); *A61B 10/04* (2013.01); *A61B 2562/166* (2013.01)

(58) Field of Classification Search
CPC ............ A61B 1/00101; A61B 1/00105; A61B 1/00124; A61B 1/0676; A61B 1/053; A61B 10/04; A61B 1/018; A61B 1/012; A61B 1/04; A61B 1/0011; A61B 1/00131; A61B 1/00137; A61B 1/00163
USPC ....... 600/104, 109, 112, 129, 153, 160, 175, 600/106–107

See application file for complete search history.

(56) References Cited

U.S. PATENT DOCUMENTS

| | | | |
|---|---|---|---|
| 9,168,057 B2 | 10/2015 | Poulsen | |
| 9,504,512 B2 | 11/2016 | Poulsen | |
| 10,610,290 B2 | 4/2020 | Bjorn-Rasmussen et al. | |
| 10,722,283 B2 | 7/2020 | Larsen | |
| 10,835,303 B2 | 11/2020 | Poulsen | |
| 11,213,195 B2 | 1/2022 | Jensen | |
| 2007/0249907 A1* | 10/2007 | Boulais | A61B 1/05 600/179 |
| 2009/0254082 A1 | 10/2009 | Kornerup et al. | |
| 2010/0191238 A1 | 7/2010 | Kornerup | |
| 2011/0184233 A1* | 7/2011 | Fructus | A61B 1/018 600/104 |
| 2012/0289858 A1* | 11/2012 | Ouyang | A61B 1/05 600/562 |
| 2014/0235943 A1* | 8/2014 | Paris | A61B 1/126 600/101 |
| 2015/0005760 A1 | 1/2015 | Poulsen | |
| 2016/0270636 A1* | 9/2016 | Iwasaka | A61B 1/00137 |
| 2016/0367119 A1* | 12/2016 | Ouyang | A61B 1/0676 |
| 2017/0078583 A1 | 3/2017 | Haggerty et al. | |
| 2017/0156575 A1* | 6/2017 | Aizenfeld | A61B 1/00128 |
| 2017/0307872 A1* | 10/2017 | Hatase | G02B 7/02 |
| 2017/0319047 A1 | 11/2017 | Poulsen et al. | |
| 2018/0132700 A1 | 5/2018 | Ouyang et al. | |
| 2018/0160893 A1 | 6/2018 | Truckai et al. | |
| 2018/0184892 A1* | 7/2018 | Truckai | A61B 1/00042 |
| 2019/0090847 A1* | 3/2019 | Yamamoto | A61B 8/44 |
| 2019/0282070 A1* | 9/2019 | Vilhelmsen | A61B 1/00103 |
| 2019/0298161 A1 | 10/2019 | Jensen | |
| 2020/0221931 A1 | 7/2020 | Wilder et al. | |
| 2020/0390316 A1* | 12/2020 | Hosogoe | A61B 1/00101 |
| 2022/0249194 A1 | 8/2022 | Harrekilde-Petersen | |
| 2022/0330807 A1 | 10/2022 | Madsen et al. | |
| 2023/0141540 A1 | 5/2023 | Worsoe et al. | |

FOREIGN PATENT DOCUMENTS

| | | |
|---|---|---|
| EP | 1150616 | 9/2005 |
| EP | 0930047 | 1/2008 |
| EP | 3860485 | 8/2021 |
| JP | 2014-521373 | 8/2014 |
| JP | 2018-531058 | 10/2019 |
| WO | WO 2021/048367 | 3/2021 |

OTHER PUBLICATIONS

The International Preliminary Report on Patentability for International Application No. PCT/US2020/021133, dated Oct. 14, 2021.

* cited by examiner

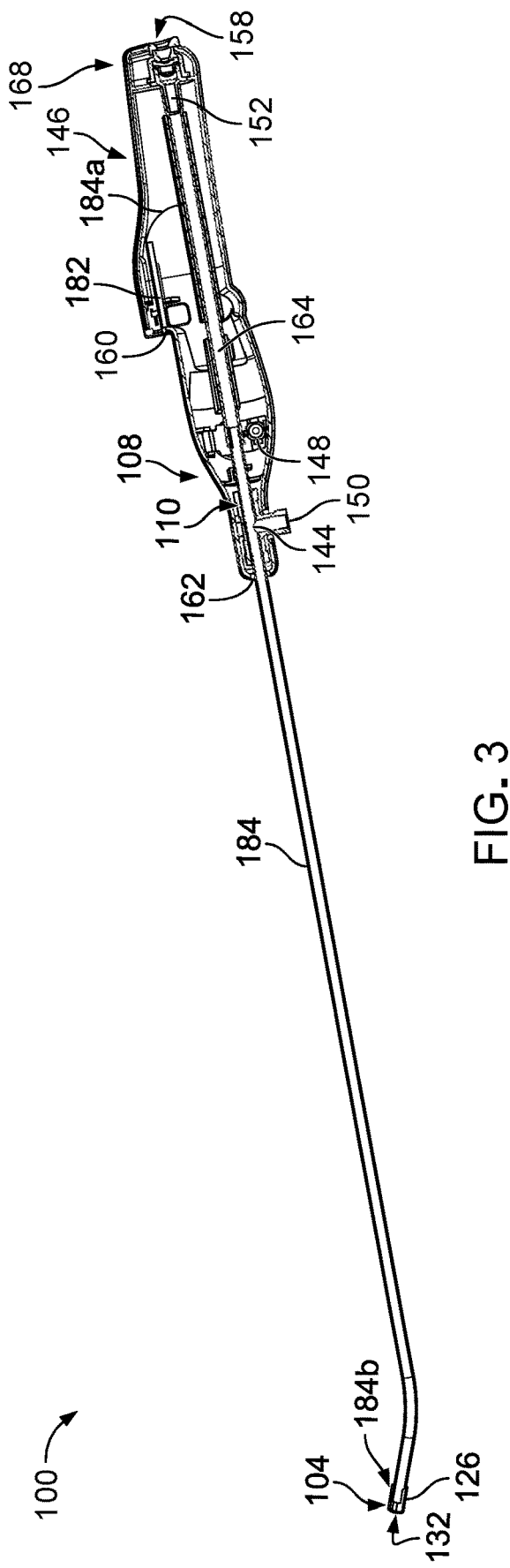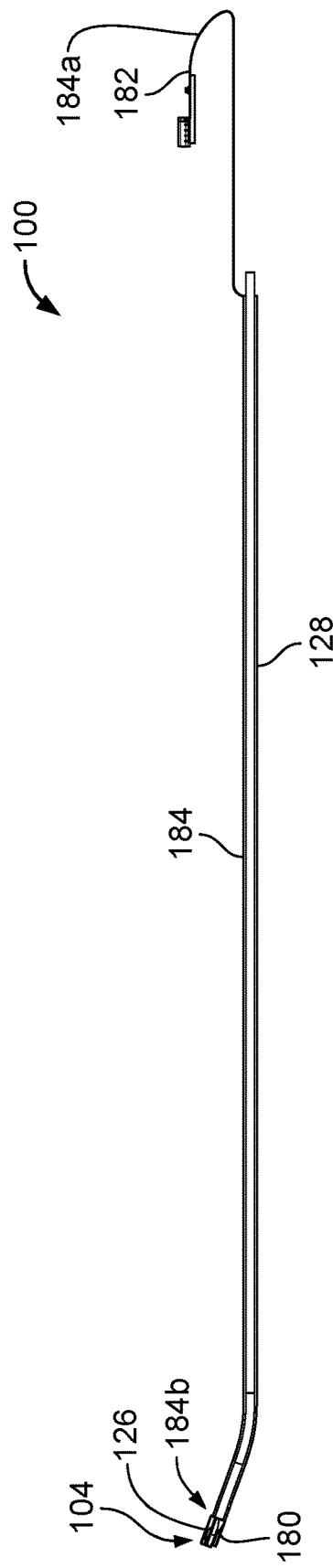

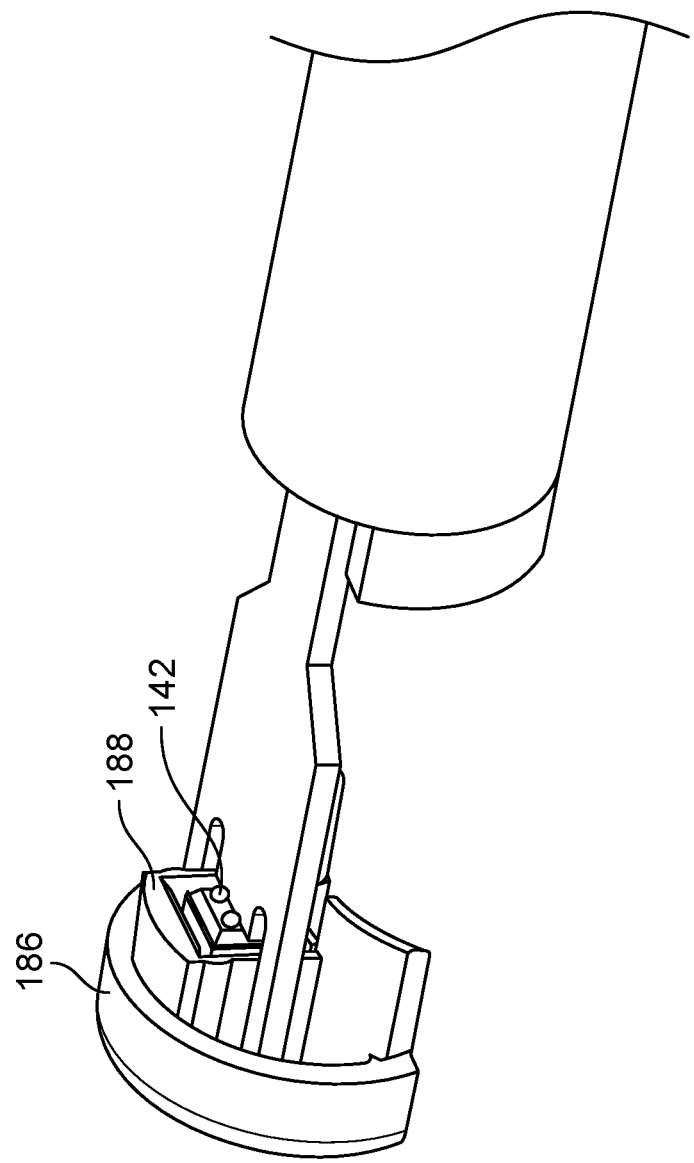

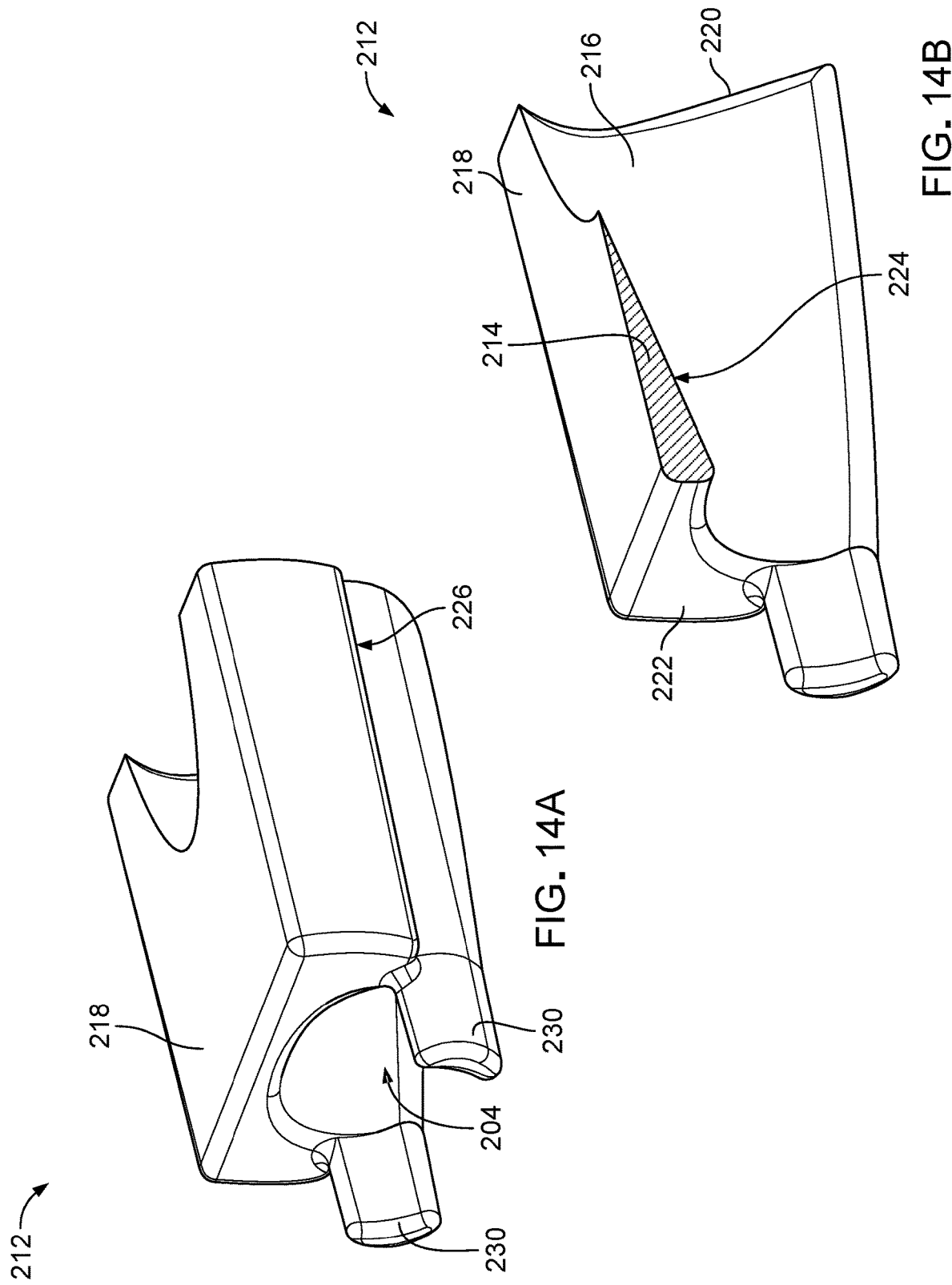

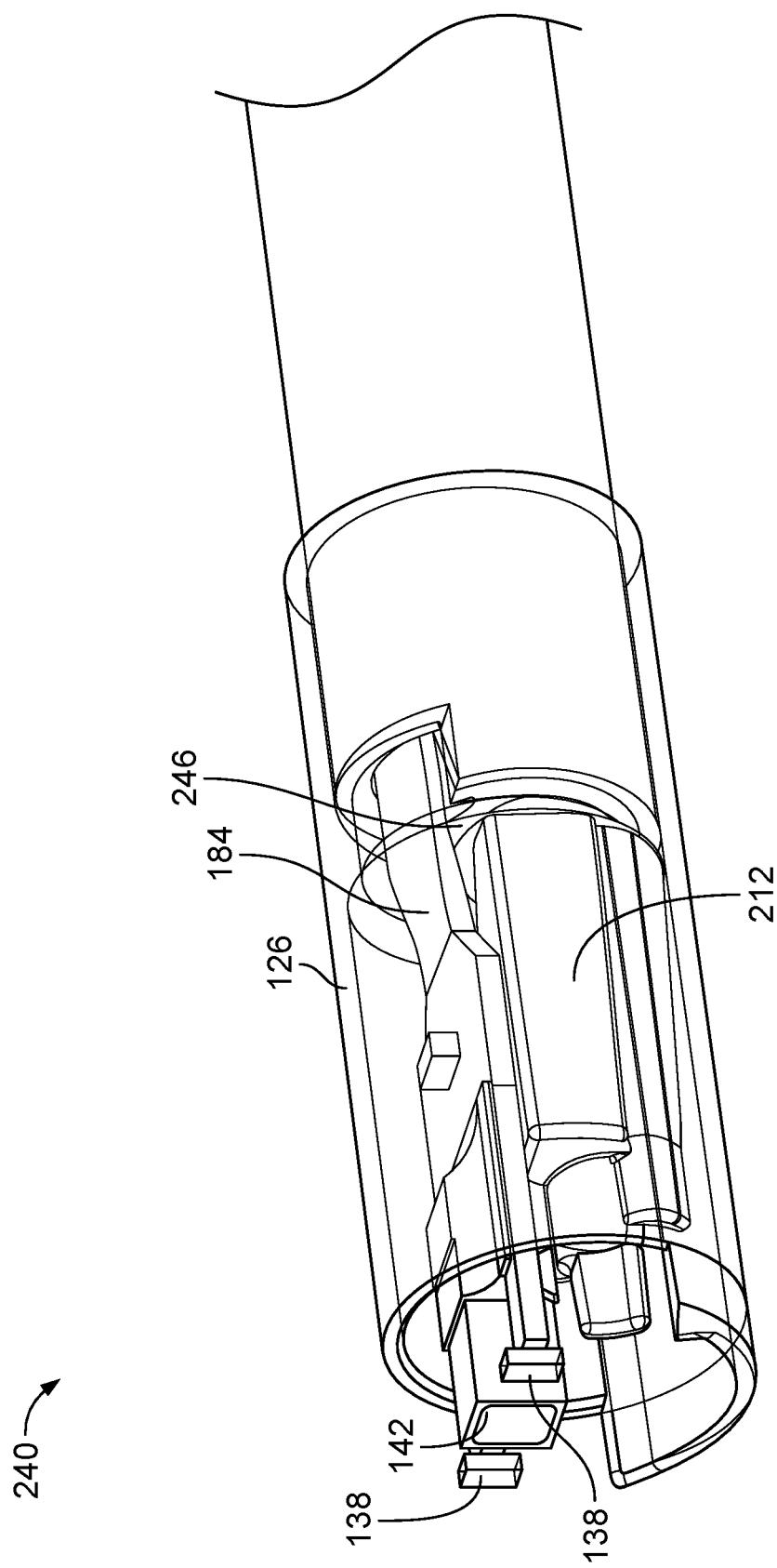

ENDOSCOPIC DEVICES AND RELATED METHODS

CROSS REFERENCE TO RELATED APPLICATIONS

This application claims the benefit of prior U.S. Provisional Application No. 62/825,962, filed on Mar. 29, 2019, which is incorporated herein by reference in its entirety.

TECHNICAL FIELD

This disclosure relates to endoscopic devices and related methods.

BACKGROUND

A hysteroscope is an endoscope that is designed for examining a patient's uterus (e.g., a uterine cavity). A hysteroscope typically includes a proximal portion that remains external to the patient's body during use and a distal portion that is inserted into the patient's uterus. The distal portion may include a tip that is sized to be inserted through the cervix and into the uterus to view the uterus, while the proximal portion provides features for manipulating the distal portion. Images captured at the tip of the distal portion can be viewed by a physician to examine the uterine cavity. Once examination has concluded, the distal portion of the hysteroscope is withdrawn from the uterus through the patient's cervix.

SUMMARY

This disclosure relates to endoscopic devices and related methods. Such endoscopic devices can be used for viewing and/or performing a surgery on a patient's uterus.

In one aspect, an endoscopic device includes a housing, a cannula configured for insertion through a cervix into a uterus, the cannula having a lumen that extends from a proximal end of the cannula to a distal end of the cannula, the proximal end of the cannula being secured within the housing, an imaging system located at a distal end of the cannula, and a flexible printed circuit (FPC) that extends within the lumen of the cannula and electrically connects the camera and the LEDs to electrical components located in the housing. The imaging system includes a camera, and one or more light-emitting diodes (LEDs) configured to provide light for the camera to acquire images of the uterus. The lumen is configured to provide a passage for a working tool.

Embodiments may include one or more of the following features.

In some embodiments, the cannula defines a proximal opening and a distal opening, the proximal and the distal openings being configured to allow a working instrument to enter the lumen via the proximal opening and exit the lumen via the distal opening.

In certain embodiments, the electrical components in the housing includes at least one of a printed circuit board (PCB), a display, a display cable, and an electrical connection port.

In some embodiments, the FPC is shaped to conform with the inner surface of the lumen. In some embodiments, the FPC is positioned within an upper third portion of the lumen.

In certain embodiments, the lumen is configured to receive a working tool that has a size of 5 French or smaller.

In some embodiments, the device further includes a tip element that holds the camera and the one or more LEDs at the distal end of the cannula, the tip element being configured to block light from entering a sensor of the camera.

In some examples, the tip element is configured so that the sensor senses substantially only reflected LED lights. The tip element can include a partitioning wall that separates the camera from the one or more LEDs. In some examples, the partitioning wall extends from a lens of the camera to a proximal end of the camera where the camera connects to the flex circuit.

The tip element can have a convex shape projecting outward from the distal end of the cannula. The tip element can form at least a portion of a tool channel configured to guide the working tool to exit the endoscopic device. The tool channel can have a curved inner surface that projects outward towards the camera.

In some embodiments, the device further includes a tip element that holds the camera and the one or more LEDs at the distal end of the cannula; and a coupler located between the tip element and a shaft that forms the lumen, the coupler having a notch that fits into a notch of a distal tip of the shaft to prevent the coupler from rotating relative to the distal tip. In some examples, the coupler has a thread formed by a bulge in the inner surface of the coupler, the thread being located at about a location where the coupler meets the distal tip of the shaft.

In some embodiments, the device further includes a tip element that holds the camera at the distal end of the cannula, the tip element being in contact with the FPC through a ramp-shaped element configured to protect electrical contacts of the camera to the FPC from potential impacts caused by a working tool passing through cannula towards the distal end of the cannula.

In some examples, the ramp-shaped element includes an adhesive material that secures the ramp-shaped element to the FPC. The ramp-shaped element can be cured by UV light to form a hard element.

In some embodiments, the ramp-shaped element includes a molded element that is positioned between the tip element and a distal end of a shaft of the cannula, wherein the shaft defines the lumen of the cannula. The device can further include a coupler element located between the distal end of the shaft and the tip element, the coupler element extending along the FPC and surrounding a distal portion of the FPC and the molded element.

In certain embodiments, the molded element has an outer surface that includes one or more groves that receive one or more ribs of an inner surface of the coupler. The coupler can have an inner surface that includes one or more ribs disposed in one or more groves of an outer surface of the molded element. In certain embodiments, the molded element has an inner surface that drafts down in diameter as the molded element extends towards the tip element. The coupler can have an inner surface that drafts down in diameter as the coupler extends towards the tip element.

In certain embodiments, the cannula is a double-lumen cannula comprising a first lumen and a second lumen, both the first and the second lumen extending along the cannula and being separated by a wall. In some examples, the FPC passes through the first lumen and the working tool passes through the second lumen.

Particular embodiments of the subject matter described in this specification can be implemented so as to realize one or more of the following advantages. Reducing the size of an endoscopic device plays a significant role in reducing stress on the patients during an examination. Certain embodiments of the present disclosure provide a single lumen cannula that provides a passage for fluids (e.g., saline), a working tool, and electronic cables. Flexible printed circuits (FPC) used in the present disclosure provide reliable electrical communications between the distal tip and the proximal region of the endoscopic device. The FPC is also small enough to leave room for a working tool and fluids to pass through the lumen.

The small size of the endoscopic device's cannula diameter and tip causes the working tool to be very close to and potentially hit the camera and the soldered joint that secures the camera to the FPC. To reduce the risk of the working tool contacting the soldered joint and/or the camera, some embodiments of the present disclosure include a ramp element that guides the working tool away from the soldered joint and the camera. The ramp element can also be designed to reduce in diameter and provide a more effective control of the working tool. Controlling the working tool improves accuracy in placing the working tool in desired locations within a patient's body for examination and operation purposes. The distal end of the endoscopic device may reduce in diameter along with the ramp element to provide a narrower tip. Such a narrow tip allows an easier and smoother penetration through body cavities.

The LEDs located at the distal tip of the endoscopic device illuminate the patient tissues so that the camera (which is also located at the distal tip) can take images of the tissues. It is desired to block light from entering the camera sensors from other directions and from sources other than the LEDs. Coating the camera and its sensors can be effective, but may result in an in consistent light blockage. In addition, a coating may easily get scratched, for example, by the working tool that passes through the cannula and exits the distal tip of the device. Implementations of the present disclosure provide a housing for the camera. The housing has walls that surround the camera and substantially blocks lights that may enter the camera sensor from the camera surroundings. The walls cover all faces of the camera except a distal face that captures images and a proximal face that is soldered to the FPC. While coating may still be used to increase light blockage, the housing provides a more uniform and reliable light blockage and reduces a risk of scratches on the coatings.

It is appreciated that systems and methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

FIG. 3 is a side cross-sectional view of the endoscopic device of FIG. 1.

FIG. 4 illustrates a cannula and a flexible printed circuit of the endoscopic device of FIG. 3.

FIG. 8 illustrates a tip element at the distal end of the endoscopic device illustrated in FIG. 1.

FIG. 14A illustrates a perspective view of the molded ramp element illustrated in FIGS. 13A-13E.

FIG. 14B illustrates a cross sectional view of the molded ramp element of FIG. 14A.

FIGS. 15A-15B illustrate a distal end of a double-lumen cannula of an endoscopic device.

Like reference numbers and designations among the various drawings indicate like elements.

DETAILED DESCRIPTION

Figure 1:
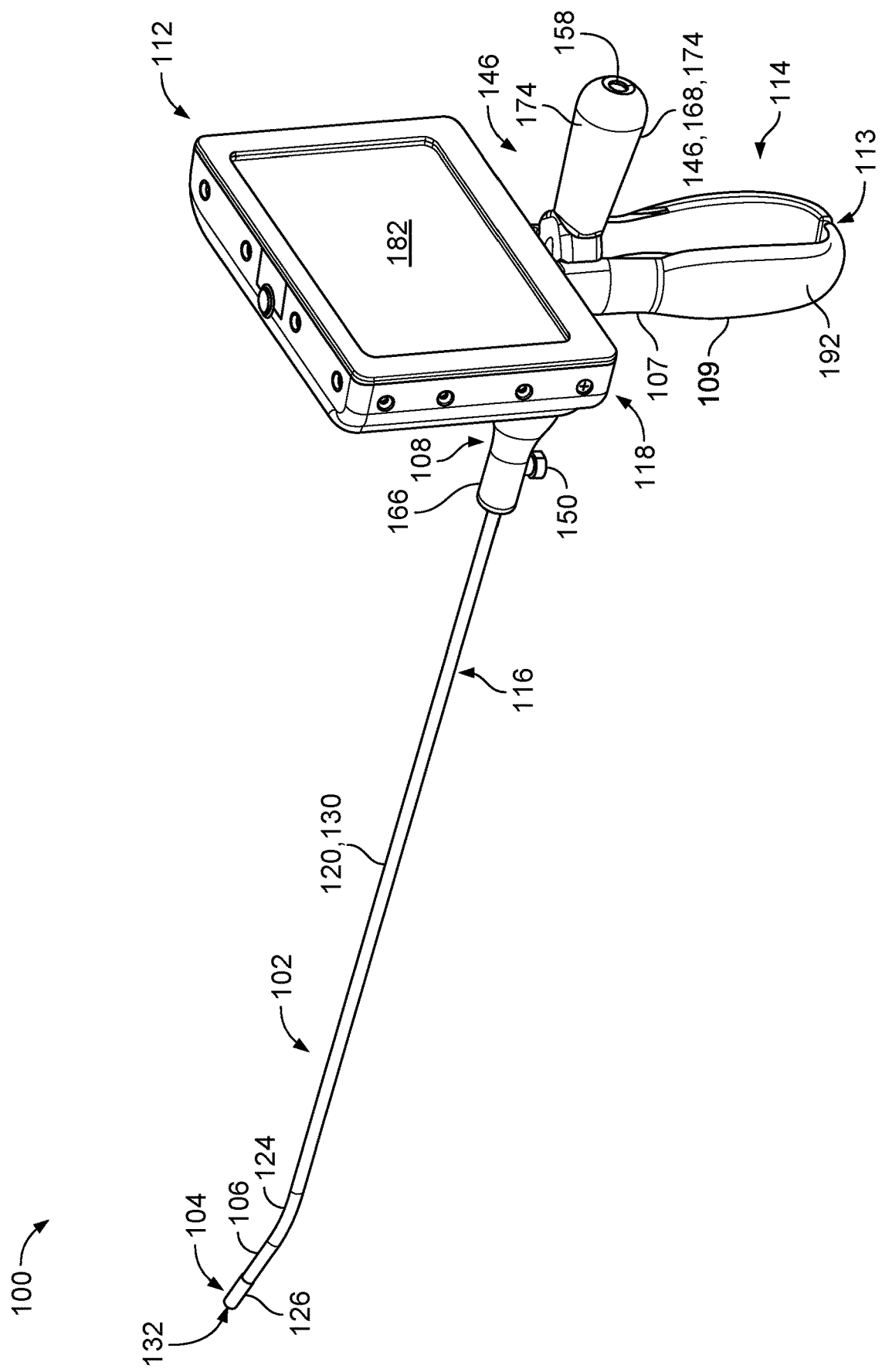
FIG. 1 is a perspective view of an endoscopic device.
Figure 2:
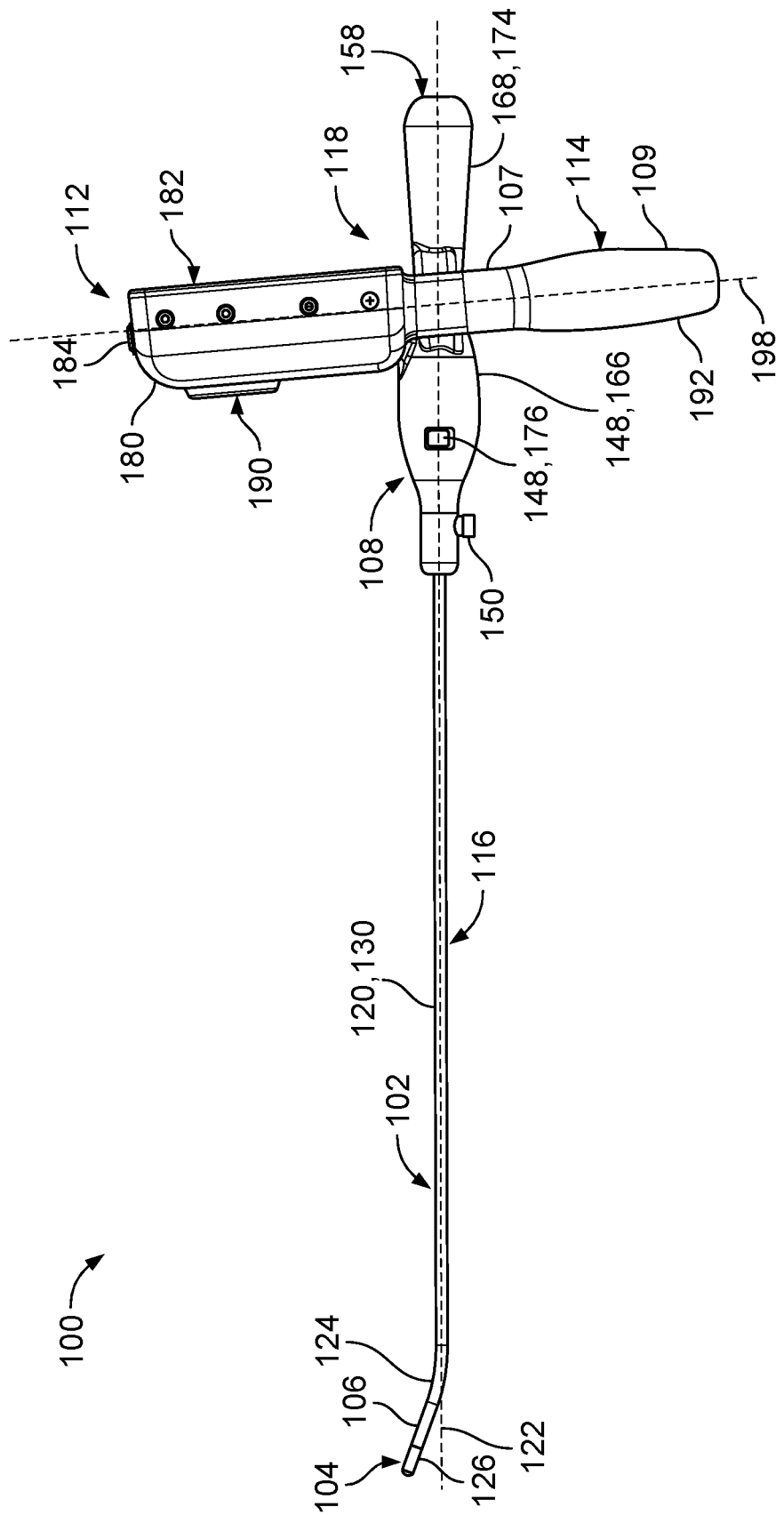
FIG. 2 is a side view of the endoscopic device of FIG. 1.

FIGS. 1 and 2 illustrate an endoscopic device 100 (e.g., a hysteroscope) that can be used to examine a patient's uterus (e.g., a uterine cavity). The endoscopic device 100 includes a cannula 102 that is formed to be inserted into a body organ such as the uterus (e.g., through a body cavity such as the patient's vaginal canal and cervix), an imaging system 104 located at a distal end 106 of the cannula 102 for imaging the uterus, and a housing 146 attached to a proximal end region 110 of the cannula 102 through a connection hub 108. The endoscopic device 100 further includes a display 112 for viewing images acquired by the imaging system 104, and a handle 114 that either extends from the display 112 (as illustrated) or is in form of a grip 174 along the housing 146.

Referring to FIGS. 1-3, the cannula 102 is an elongate, generally tubular member that is sized to pass through a cervix into a uterus. The cannula 102 includes a shaft 120 and a coupler 126 that secures the imaging system 104 to the distal end 106 of the shaft 120. The shaft 120 includes a major portion 130 (e.g., including the proximal end region 110) with a central axis that defines a primary axis 122 of the cannula 102, the distal end 106, and a distal bend 124 that connects the major portion 130 to the distal end 106.

The shaft 120 defines a lumen 128 that houses one or more electrical cables of the imaging system 104, that allows for passage of fluids between the distal end 106 and the connection hub 108, and that allows for passage of a working tool. The passage extends distally from the proximal end region 110 of the cannula 102 to the distal end 106 of the cannula. The shaft 120 further defines a sidewall opening 144 along the proximal end region 110 through which fluid can be delivered to the lumen 128 or withdrawn (e.g., suctioned) from the lumen 128 (see FIG. 3).

The working tool can be used for surgery or biopsy purposes. The working tool can enter the endoscopic device 100 through a proximal opening 158 of the housing 146 (see FIGS. 1 and 3), pass through an operative channel 164 and the cannula 102, and exit through a luminal opening 132 at the coupler 126. The working tool enters the endoscopic device 100 through the proximal opening 158 of the housing 146 (see FIGS. 1 and 3), passes through the operative channel 164 and the cannula 102, and exits through the luminal opening 132. Example working tools that can be passed through the operative channel 164 include various biopsy instruments (e.g., forceps, graspers, and scissors) having a size of 5 French or smaller. For example, the working tool can have an outer diameter of 1.6 millimeter or smaller.

The electrical cables of the imaging system 104 within the lumen 128 include one or more flexible printed circuits (FPC). FIG. 3 illustrates an FPC 184 that extends within the lumen 128 and electrically connects the imaging system 104 to electrical components located in the housing 146. The electrical components in the housing 146 can include a PCB or ROM 182, a camera actuator 148, a display cable, a connection port 160 (e.g., a micro HDMI port or other types of port) to which the display 112 or the display cable can be connected, etc.

The FPC 184 has a proximal portion 184a and a distal portion 184b. The housing 146 is removed in FIG. 4 to illustrate the proximal portion 184a more clearly. The proximal portion is connected to a PCB or ROM 182. The FPC 184 extends from the proximal portion 184a to the distal portion 184b along the lumen 128. The FPC 184 is positioned within an upper third portion of the lumen 128. The FPC 184 can be shaped (e.g., be bent) to conform with the inner surface of the lumen 128.

Figure 5A:
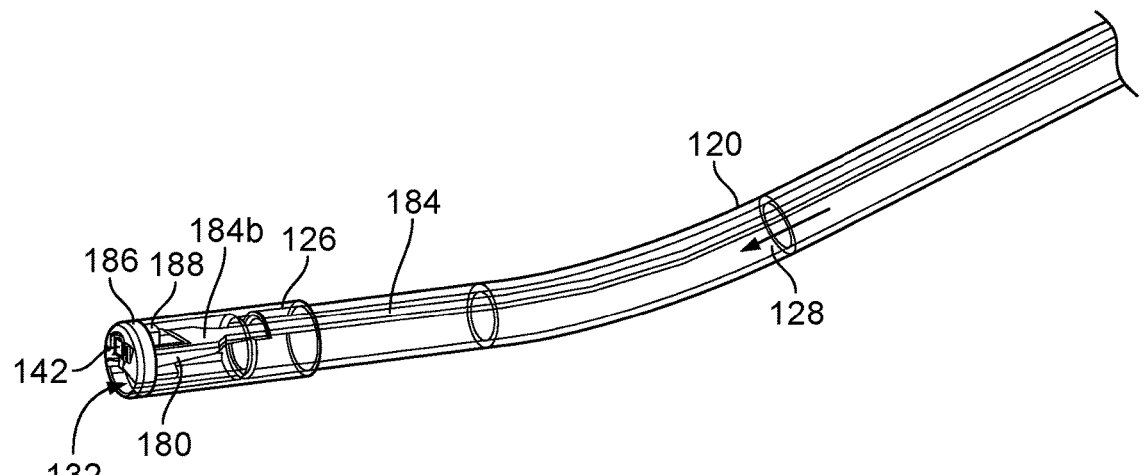
FIGS. 5A-5B are perspective views of several components of a distal end of the endoscopic device of FIG. 1.
Figure 5B:
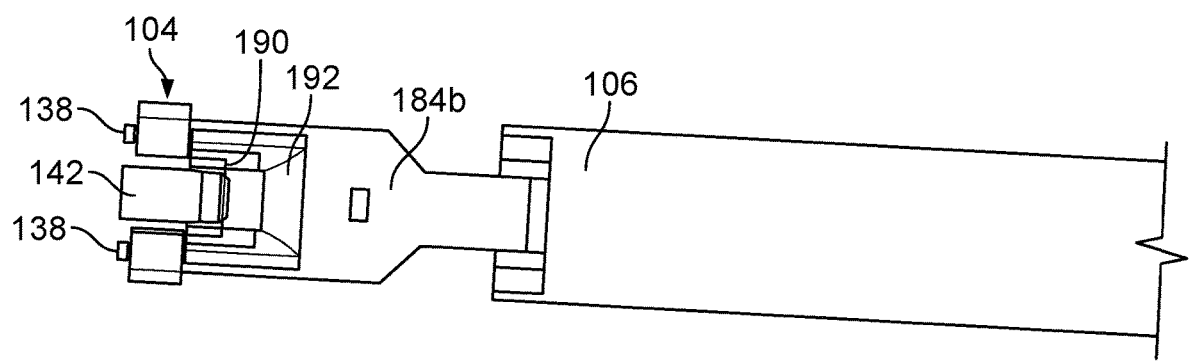

FIGS. 5A and 5B illustrate the distal portion 184b of the FPC 184. The distal portion 184b is electrically connected to the imaging system 104. The imaging system includes a camera 142 and one or more light emitting diodes (LEDs) 138. The LEDs 138 are located on opposite sides of the camera 142 to evenly illuminate surrounding tissues for image acquisition.

FIG. 5B is a top view of the distal portion 184b. The coupler 126 is removed in FIG. 5B to illustrate the electrical connections between the distal portion 184b of the FPC 184 and components of the imaging system 104. As illustrated, the camera 142 is soldered to an edge 190 of the distal portion 184b of the FPC 184. An adhesive material 192 covers the soldered region to protect the soldered joint from movement and to prevent unwanted disconnections of the electrical connection between the camera and the FPC 184. The adhesive material can be an epoxy of any color, or a clear epoxy.

Figure 6:
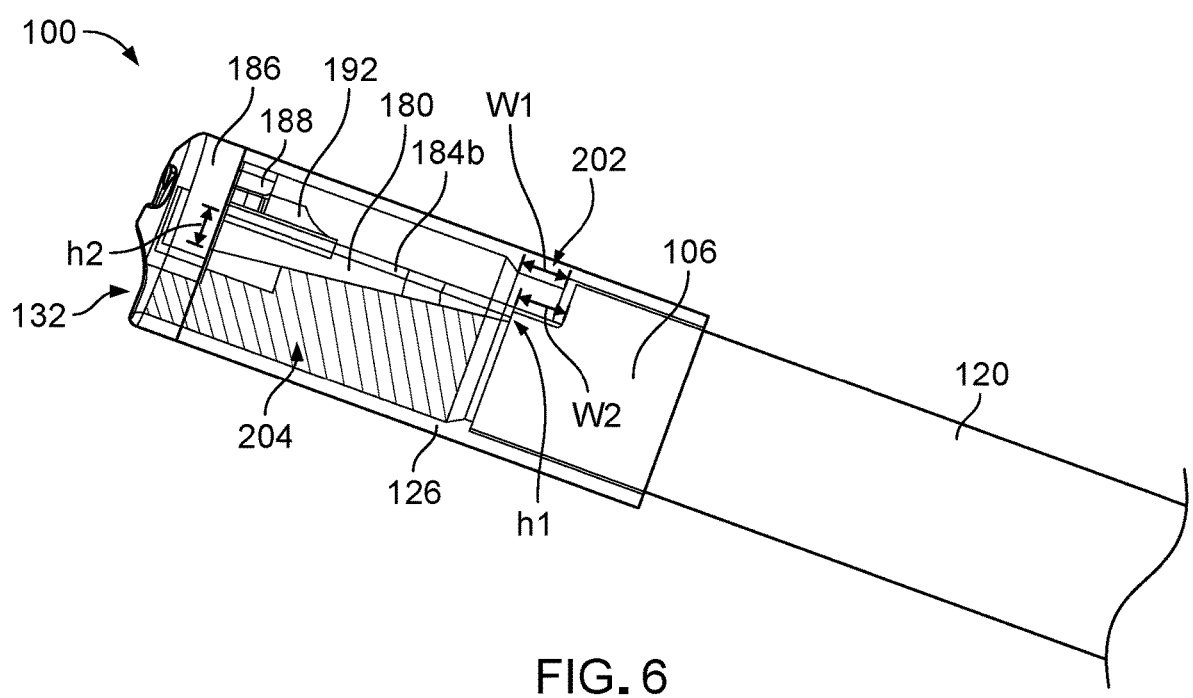
FIG. 6 illustrates a perspective view of a coupler at the distal end of the endoscopic device of FIG. 1.
Figure 7:
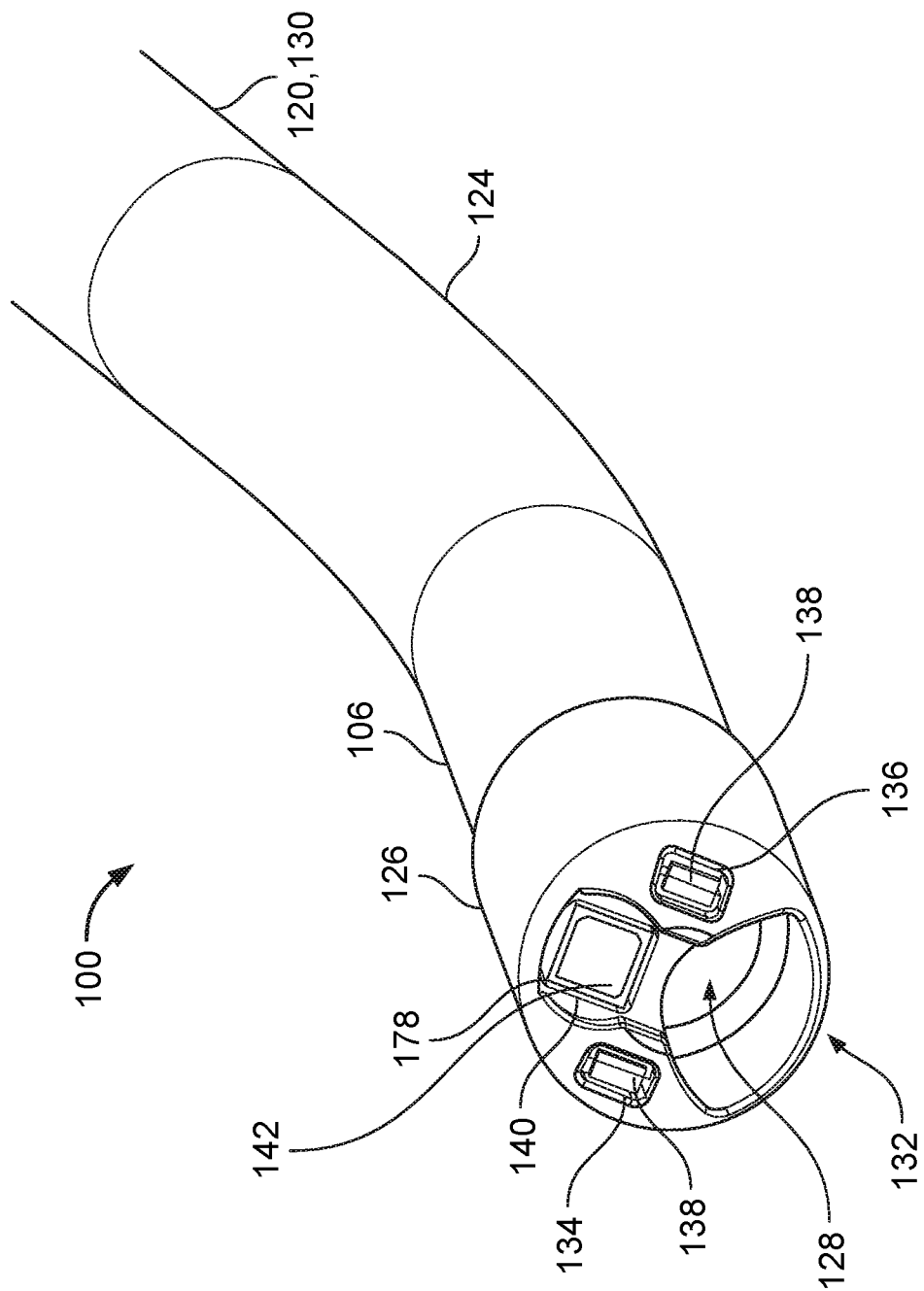
FIG. 7 illustrates a perspective view the distal end of the endoscopic device of FIG. 1.

FIG. 6 illustrates a side view of a distal end of the endoscopic device 100, including the coupler 126 secured to the distal end 106 of the shaft 120. The coupler is connected to a tip element 186. FIG. 7 illustrates the tip element 186 at the distal end of the endoscopic device. The tip element defines (at least part of) a luminal opening 132 (e.g., a forward facing fluid port) through which fluids and uterine tissue (e.g., endometrial tissue) can enter and exit the lumen 128 of the shaft 120. The tip element also includes two lateral openings 134, 136 in which LEDs 138 are disposed, and a recessed opening 140 in which the camera 142 is disposed.

The FPC 184 extends from the connection port 160 and/or the PCB 182 to the camera 142, the LEDs 138 and other electrical components that provide electrical communication amongst the various components of the imaging system 104.

The luminal opening 132 at the tip element 186 of the coupler 126 allows fluid (e.g., a saline solution, a hypotonic solution, or an isotonic fluid) to exit the distal end 106 to flow into the uterus and to push tissue or other particulate matter away from the camera 142 so as to improve a quality of images acquired by the camera 142. For example, the luminal opening 132 can be useful in clearing away tissue debris that may collect on the distal end of the endoscopic device and otherwise impair imaging due to an overly bright appearance of the debris as light reflects from the debris. In some cases, the luminal opening 132 can also facilitate insertion of the cannula 102, as fluid exiting the luminal opening 132 may lubricate and partially distend tissues surrounding the distal end 106. In this manner, the luminal opening 132 can reduce a risk of accidental damages to the vaginal cavity, to the cervix, or to the uterus during insertion of the cannula 102 into the patient.

The luminal opening 132 is sized to permit passage of one or more working tools (e.g., a 5 French or smaller biopsy tool). For example, the luminal opening 132 typically has a cross-sectional area of about 0.03 $cm^2$ to about 0.05 $cm^2$ and is about 50% to about 80% of a cross-sectional area of the lumen 128, itself.

Fluid solution enters the cannula through either the entry port 152 disposed at the proximal opening 158 of the housing 146, or a fluid port 150 located adjacent the proximal end region 110 of the cannula 102. The fluid port 150 is formed as a T-connection and is typically made of one or materials including polycarbonate, ABS, or polypropylene. One benefit of introducing fluid through the fluid port 150 (rather than through the proximal opening 158) is that introducing the fluid would not interrupt entering or operation of the working tool. The fluid port 150 is formed to engage fluidic devices (e.g., syringes or extension tube sets) for delivering fluid to or withdrawing fluid from the lumen 128 of the cannula 102.

As noted above, the tip element 186 includes two lateral openings 134, 136 in which LEDs 138 are held and disposed, and a recessed opening 140 in which the camera 142 is held and disposed. The tip element 186 can be designed to substantially block light from entering a sensor of the camera 142.

FIG. 8 illustrates a shield (or housing) 188 of the tip element 186. The shield 188 surrounds the camera 142 to substantially block the light so that the camera sensor senses only reflected LED light. The shield 188 extends from a distal end of the camera 142 (for example, from the lens of the camera) to a proximal end of the camera 142 where the camera is soldered to the FPC 184. The shield 188 has a partitioning portion 188a that separates the camera 142 from the LEDs 138. The shield includes walls that cover all faces of the camera except a distal face that takes images and a proximal face that is soldered to the edge 190 of the FPC 184.

The tip element can be a molded solid material made of a polymer, for example, liquid crystal polymer (LCP). The tip can be black to prevent light leakage from the shield 188 into the camera sensors.

Figure 9A:
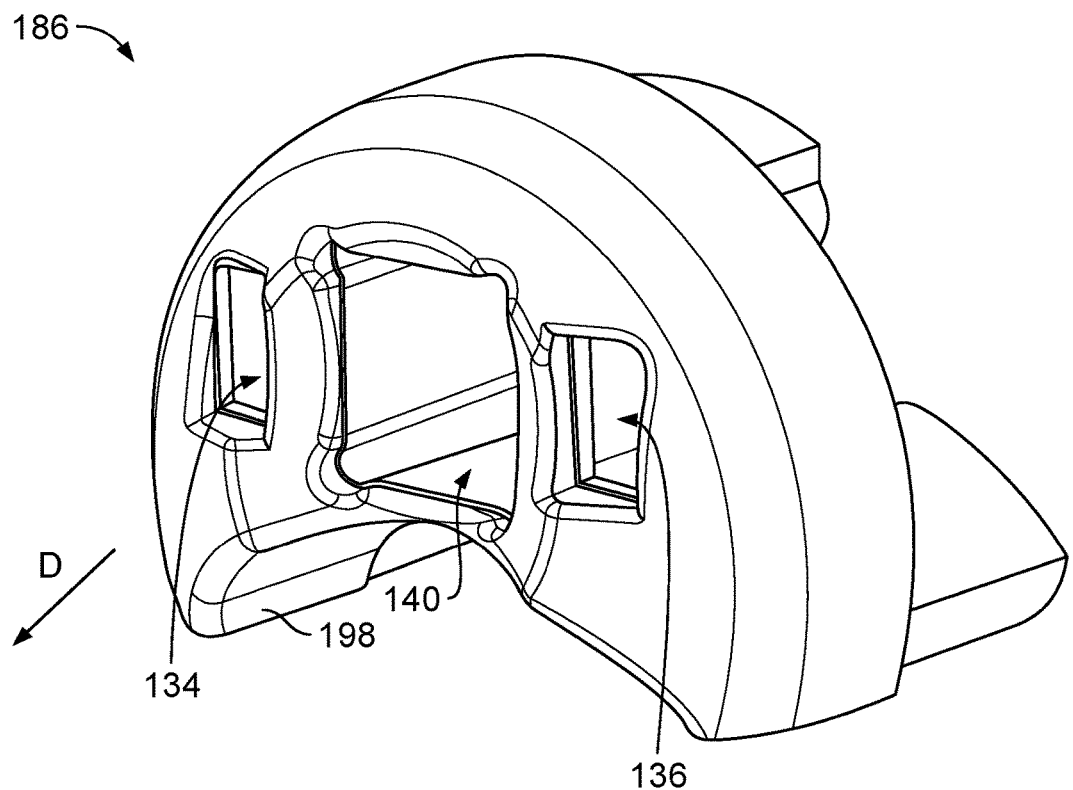
FIGS. 9A-9B illustrate perspective views of the tip element illustrated in FIG. 8.
Figure 9B:
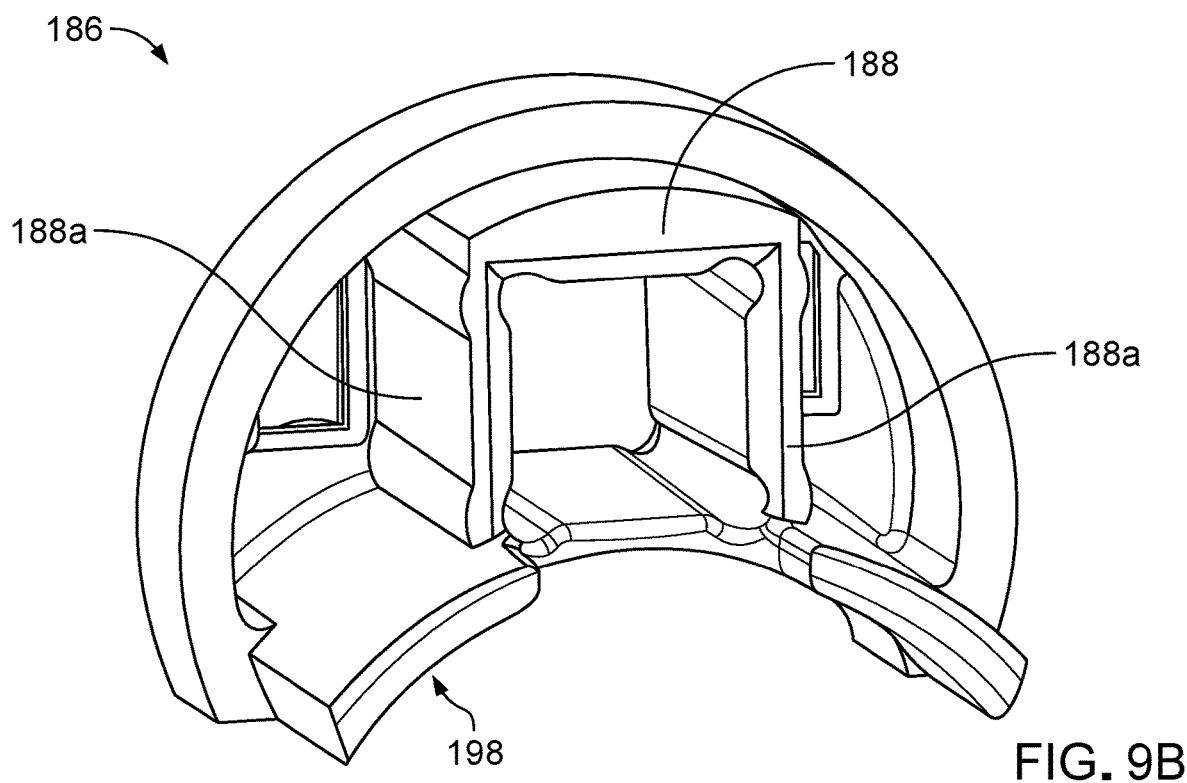

FIGS. 9A and 9B illustrate the tip element 186. The tip element 186 has a convex shape projecting outward in direction D. The convex shape is designed to allow a smooth movement of the tip element 186 through the patient's uterus cavity (or other body cavities) and reduce a likelihood of scratching or tearing the cavity.

The tip element 186 forms at least a wall of a tool channel that is configured to guide a working tool to exit the endoscopic device 100 through luminal opening 132. The wall is illustrated as an upper wall 198 in FIGS. 9A and 9B. The upper wall 198 can be curved (as illustrated), or can be straight. The upper wall 198 has a curved inner surface that projects outward towards the camera. A curvature of the upper wall 198 can be designed based on a curvature or a diameter of the working tool so as to provide enough space for the passage of the working tool. Alternatively, the tip element 186 can be designed to include other walls of the working channel as well, so as to form the whole luminal opening 132.

The coupler 126 functions as an interface between the tip element 186 and the distal end 106 of the shaft 120. The coupler 126 illustrated in FIG. 10 includes a notch 200 that locks into a notch 194 of the distal end 106 and prevents a rotation of the coupler.

The coupler 126 has an inner surface with a first dimeter at a first portion of the coupler where the coupler covers the distal end 106, and with a second diameter at a second portion of the coupler where the coupler covers the distal portion 184*b* of the FPC 184. The first dimeter may be equal, larger, or smaller than the second diameter. In some embodiments, the coupler 126 has a cylindrical outer surface. In some embodiments, the coupler's diameter varies (for example, drafts down) along the coupler.

Figure 10:
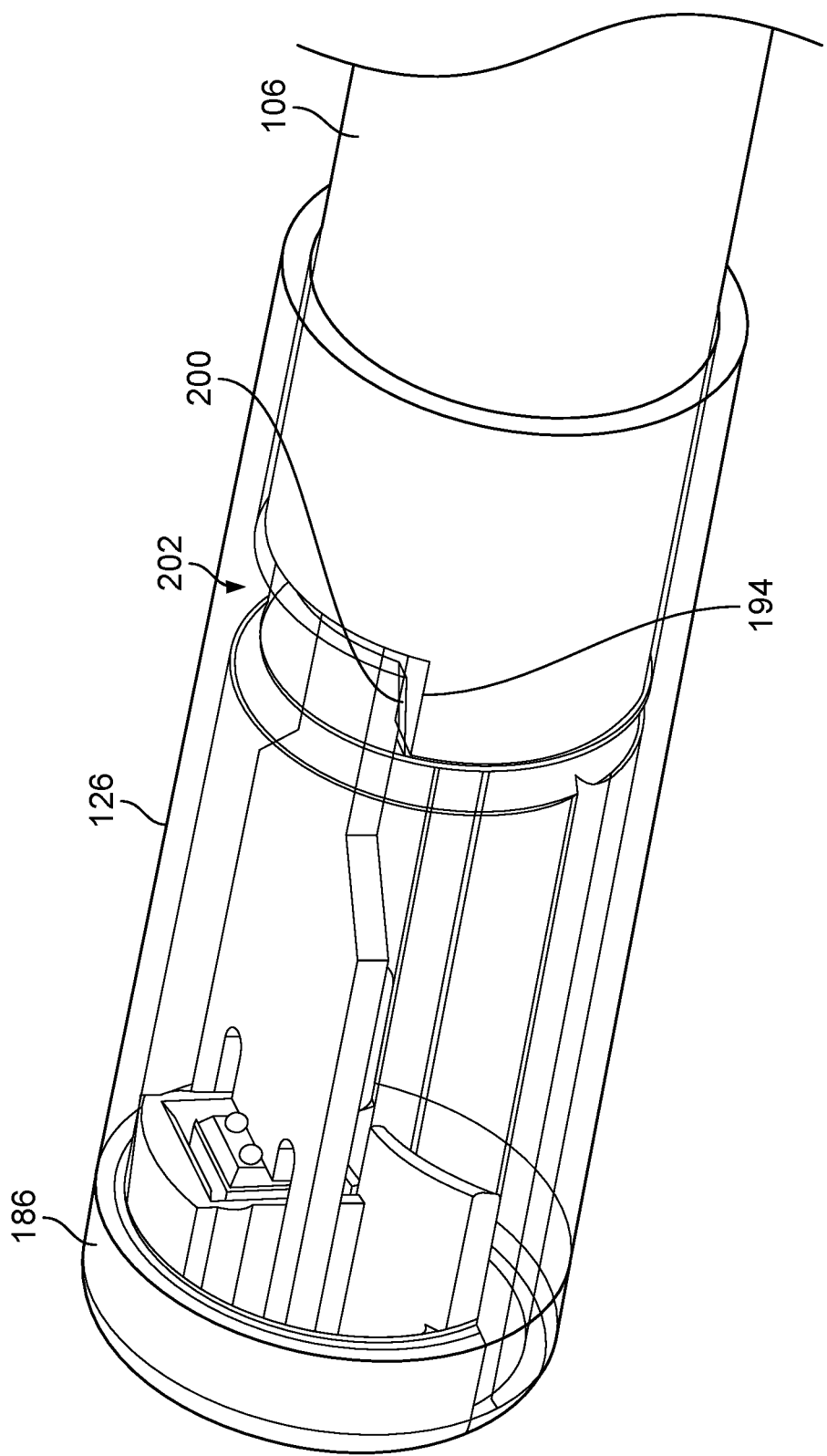
FIG. 10 illustrates contacts between the coupler illustrated in FIG. 6 and other components of the cannula illustrated in FIG. 4.

In some embodiments, the coupler 126 has a thread (receptacle, or slot) 202 that is formed as a bulge in the inner surface of the coupler, moving from the first portion to the second portion of the coupler. The thread 202 strengthens the locking feature of the notch 200. Moving from the first portion of the coupler to the second portion, the thread may have a width ($w_1$) that is substantially equal to the width ($w_2$) of the notch 200 (as shown in FIG. 10), or may have a width that is larger than (as shown in FIG. 6) or smaller than the width of the notch.

Figure 13A:
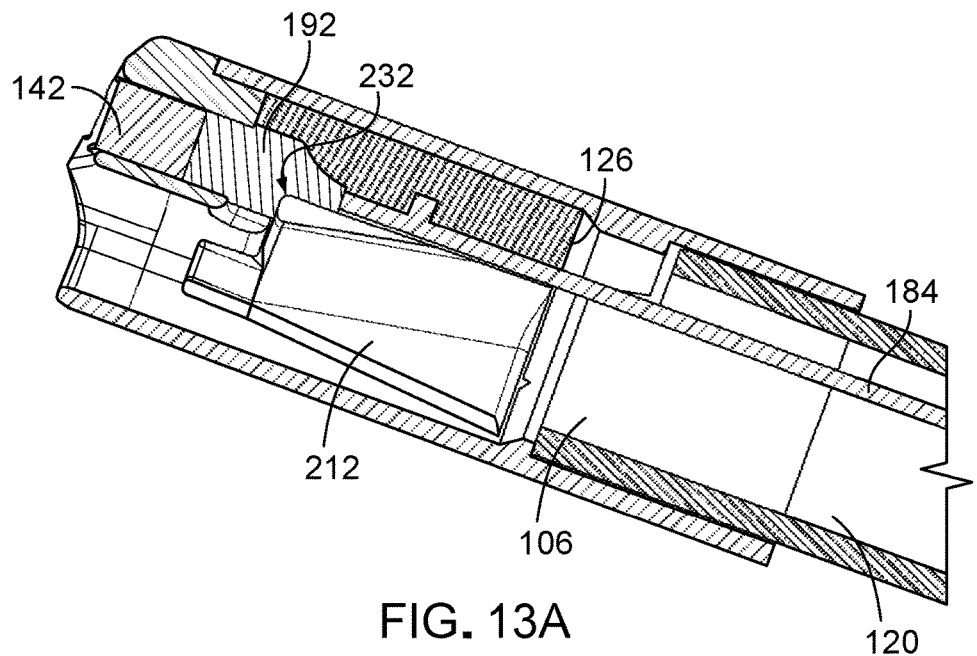
FIGS. 13A through 13E, illustrate different views of a distal end of an endoscopic device that includes a molded ramp element.

As noted above, the camera 142 is soldered to the distal portion 184*b* of the FPC 184 and the soldered region is protected by an adhesive material 192. The adhesive material 192 shown in FIG. 6 is applied on a top surface of the distal portion 184*b*. Alternatively, or in addition, the adhesive material can be applied to a bottom surface of the distal portion 184*b* (as shown in FIG. 13A).

FIG. 6 also illustrates a ramp-shaped element ("the ramp") 180 located at a bottom surface of the distal portion 184*b*. The ramp 180 is configured to protect electrical contacts of the camera to the FPC from potential impacts caused by the working tool passing through cannula towards the luminal opening 132. The ramp 180 guides the working tool away from the soldered joint.

The ramp 180 has a height that varies along the FPC's distal portion 184*b* moving towards the tip element 186. The ramp height is defined in a direction perpendicular to the FPC 184. Moving along the FPC from about the distal end 106 of the shaft 120 towards the tip element 186, a value of the height increases. As illustrated in FIG. 6, the ramp's first height (h1) proximate the distal end 106 is lower than the ramp's second height (h2) proximate the tip element 186. Such variation in the ramp height guides a working tool that passes through a tool channel 204 (hachured area) away from the adhesive material 192 and/or from the camera 142.

The ramp 180 may be secured to the bottom surface of the FPC's distal portion 184*b*, to the tip element 186, or to both. The ramp 180 may be made of one or more adhesive materials or may be secured to the FPC or the tip element by an adhesive material.

Figure 11A:
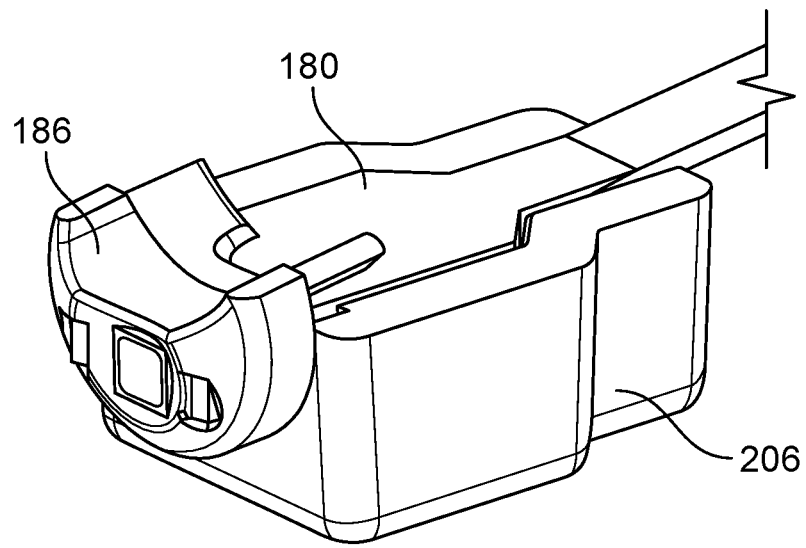
FIGS. 11A-11B illustrate a method of forming a ramp-shaped element of the endoscopic device illustrated in FIG. 1.
Figure 11B:
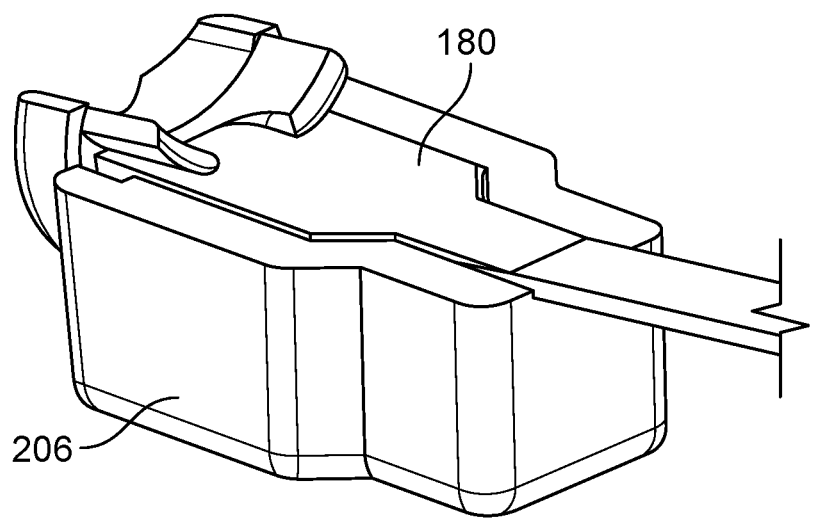

FIGS. 11A-11B illustrate a method of forming the ramp 180. In this method, an inner surface of a nest 206 is filled with an adhesives material. The inner surface has a ramp shape so that when the adhesive is hardened and detached from the nest 206, the ramp-shape element 180 is formed. Depending on the material used, the adhesive material may be hardened by leaving the adhesive material in the nest for a pre-determined period of time, or by a post-process procedure such as by exposing the adhesive material to a radiation (e.g., curing by UV light).

Figure 12A:
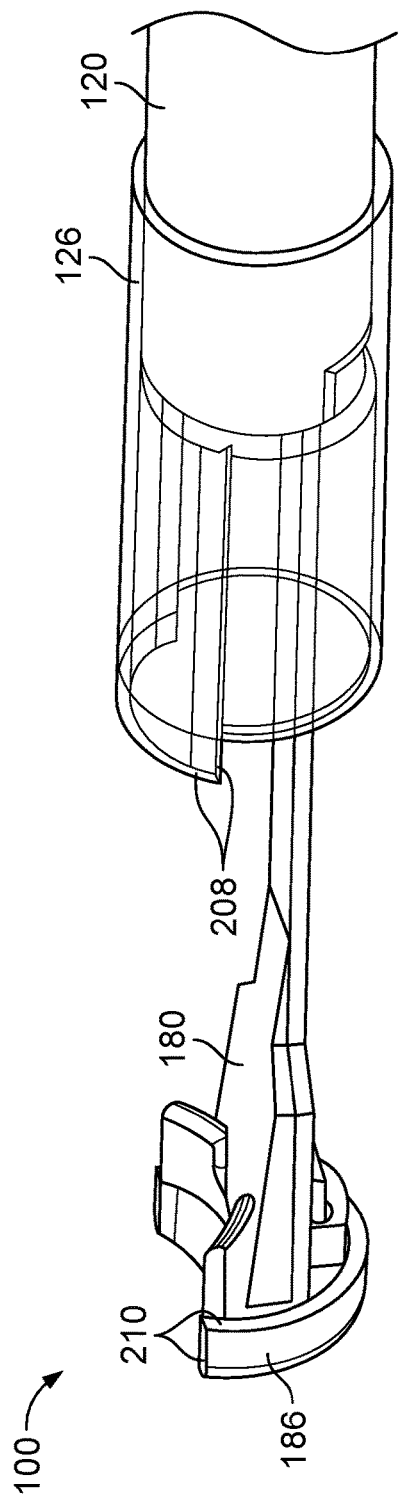
FIGS. 12A-12B illustrate a method of attaching the tip element of FIG. 8 to the coupler illustrated in FIG. 6.
Figure 12B:
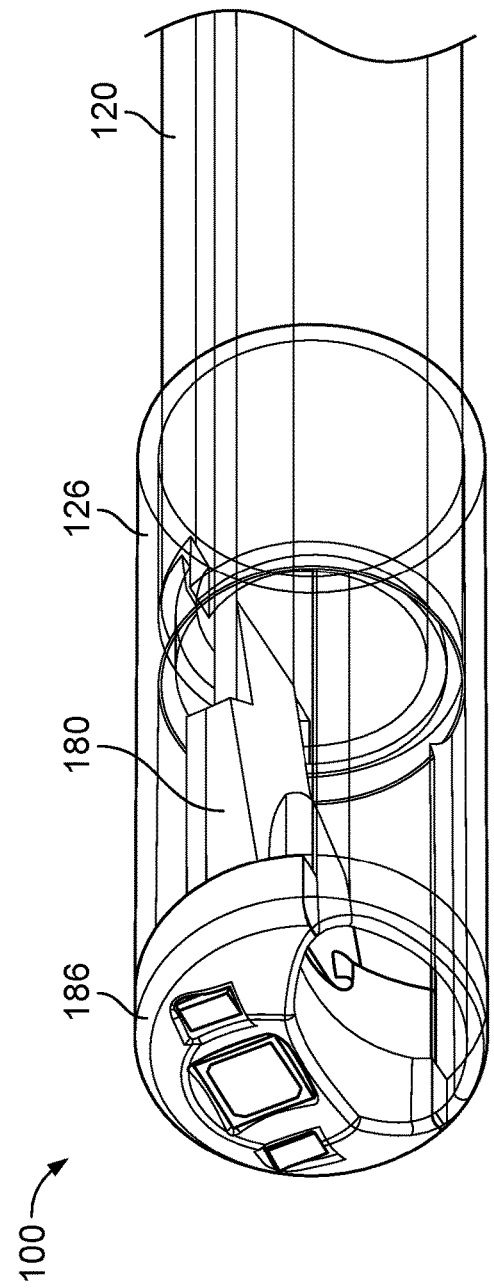

Upon forming the ramp 180, the tip element 186 along with the ramp 180 are attached to the coupler 126. FIGS. 12A and 12B illustrate a method of attaching the tip element to the coupler. The coupler 126 and the shaft 120 are moved towards the tip element 186 (FIG. 12A), and attached to the tip element 186 (FIG. 12B). In some embodiments, a contacting portion 208 of the coupler 126 has a profile that mates a contact portion 210 of the tip element. In some examples, the contact portions 208 and 210 have one or more indentation or bulges that mate each other and prevent a rotation of the coupler and the tip element.

In some embodiments, a molded ramp element is used to guide the working tool in the working channel. The molded ramp element can be manufactured in advance and be assembled on the endoscopic device.

FIGS. 13A through 13E, illustrate different views of a distal end of an endoscopic device that includes a molded ramp element 212, according to the present disclosure. The molded ramp element 212 is positioned within the coupler 126 and between the distal end 106 of the shaft 120 and the tip element 186. The molded ramp element 212 has an outer upper surface that is in contact with the FPC 184, with a portion of the adhesive material 192, or both. The molded ramp element 212 has an inner surface that drafts down in diameter as the molded ramp element extends towards the tip element 186.

Figure 13B:
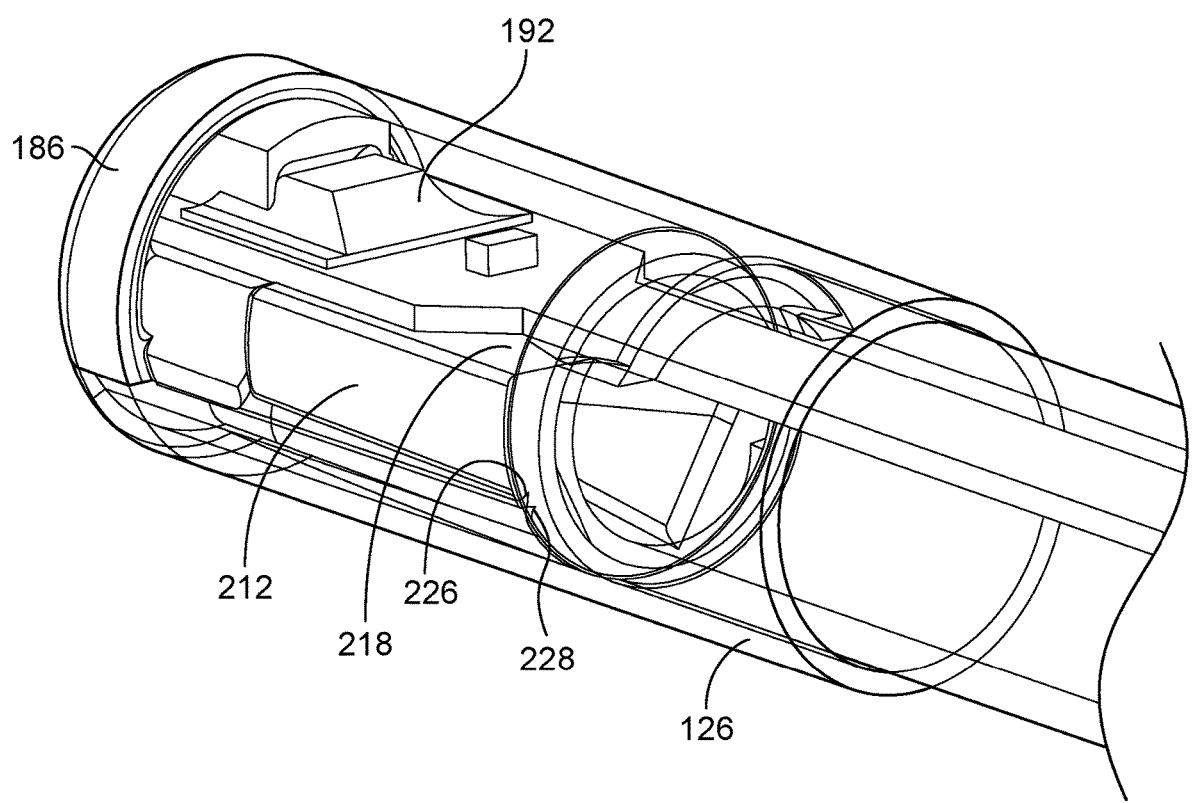
Figure 13C:
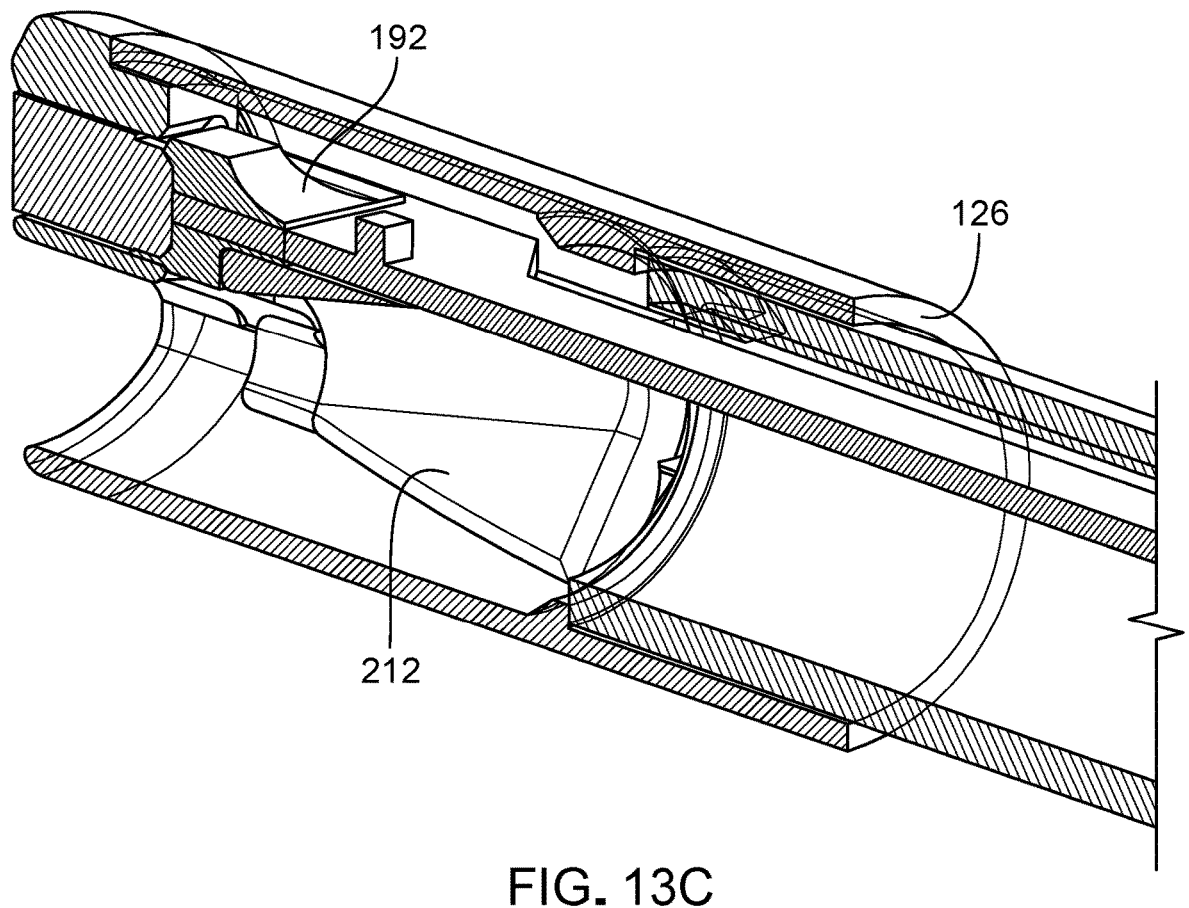
Figure 13D:
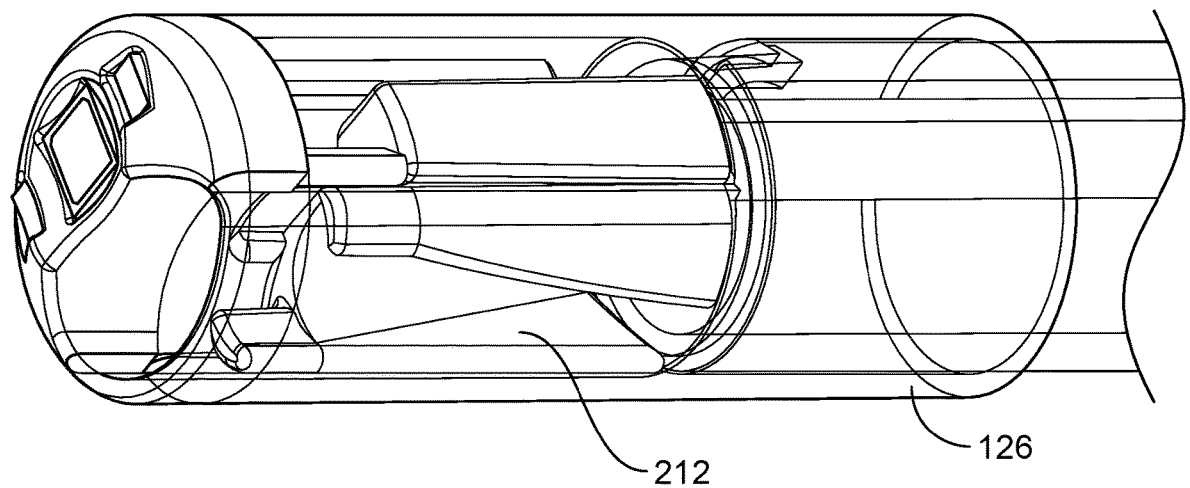

FIG. 14A illustrates an example molded ramp 212 that is used in the device of FIGS. 13A-13C. The molded ramp element 212 has a cavity that forms (at least part of) the tool channel 204 through which a working tool can pass. The molded ramp element has a flat outer upper surface 218 to support the FPC from the bottom.

FIG. 14B illustrates a cross sectional view of the molded ramp element 212. The molded ramp element 212 has an inner surface 216. Moving from a proximal portion 220 of the molded ramp element 212 to a distal portion 222 of the molded ramp, the distance between an upper portion 224 of the inner surface 216 and the outer upper surface 218 changes so that a ramp profile 214 is created on the upper portion 224 of the inner surface 216. This ramp profile is designed so that when the molded ramp element 212 is positioned between the shaft 120's distal end 106 and the tip element 186 (see FIG. 14), the ramp profile guides the working tool away from the adhesive material 192. Particularly, the ramp profile guides the working tool away from the soldered joints and the contact surface 232 of the adhesive material 192 below the FPC 184. Such design protects the soldered joint of the camera 142 from impacts of the working tool.

Figure 13E:
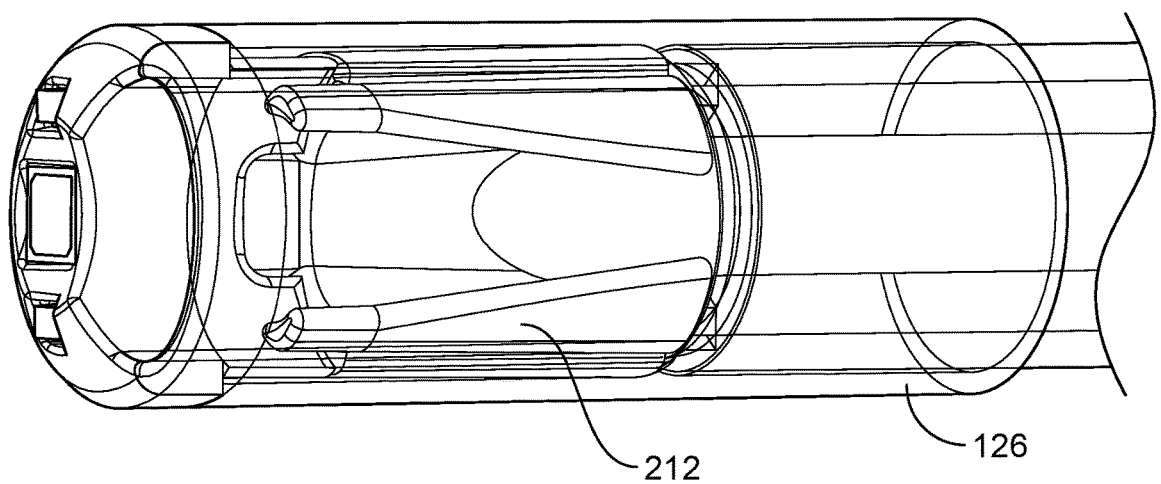

The molded ramp element 212 can be designed with surface profiles of the coupler, the tip, or both and eliminate a need to use an adhesive for attaching the molded ramp element to the FPC. For example, the molded ramp element 212 has an outer surface that includes one or more indentations (or groves) 226 that mate with one or more bulges (or ribs) 228 of an inner surface of the coupler 126 (see FIG. 13B). Alternatively, or in addition, the outer surface of the molded ramp element 212 can have one or more bulges (or ribs) that mate with one or more indentations arranged on the inner surface of the coupler 126. FIG. 13E illustrates a bottom view of the distal end of the endoscopic device and the molded ramp element 212.

The molded ramp element 212 illustrated in FIGS. 13A-14B includes two extensions 230 configured to prevent the molded ramp element 212 from rotation. Although FIGS.

13A through 14B illustrate two extensions, the molded ramp element can have any number of extensions or no extension.

Figure 15A:
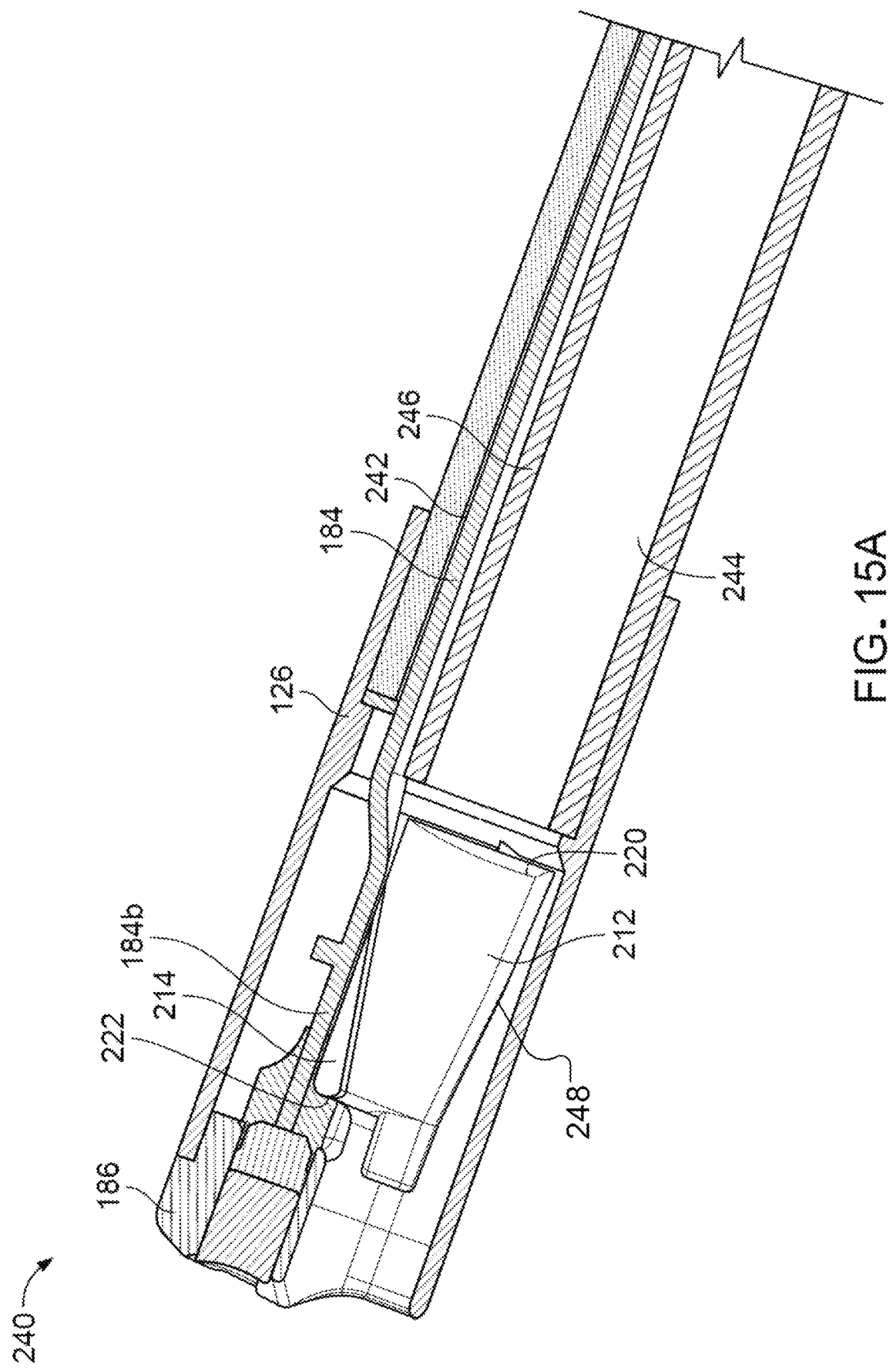

Although the endoscopic devices illustrated in FIGS. 1 through 14B have a single lumen, the endoscopic device described herein can have more than one lumen. FIGS. 15A through 15B illustrate a distal end of a double-lumen cannula 240.

FIG. 15A illustrates a cross-sectional view of the distal end of the double-lumen cannula 240. The cannula 240 has a first lumen 242 and a second lumen 244. Electrical cables such as an FPC 184 pass through the first lumen 242, while a working tool and fluids pass through the second lumen 244. The first lumen 242 is separated from the second lumen 244 by a wall 246. The wall 246 can be continuously extended along the cannula.

The tip element 186 is removed in FIG. 15B to illustrate the positions of the camera and LEDs more clearly. As illustrated, the molded ramp element 212 separates the passage of the working tool from the FPC 184 within the coupler 126 so that the working tool exits from the luminal opening 132 without contacting the camera 142 or the LEDs 138.

Depending on the size of the working tool, the molded ramp element 212 can be designed to draft down in diameter as the molded ramp element extends towards the tip element 186. The molded ramp element 212 has a ramp-shaped lower surface 248. Moving from the proximal portion 220 of the molded ramp element 212 to its distal portion 222, the lower surface 248 inclines towards the ramp 180 (see FIG. 15A). A molded ramp element with a ramp-shaped lower surface allows a more effective control of the working tool and thus, improves accuracy in placing the working tool in desired locations within a patient's body.

In some embodiments, the coupler 126 drafts down in diameter along the molded ramp element 212's lower surface 248. Such coupler provides a narrower tip for the endoscopic device, which allows an easier and smoother penetration through body cavities.

Referring back to FIGS. 1-2, the connection hub 108 can also provide several features for fluid and electrical communication between the proximal end region 110 of the cannula 102 and the distal end 106 of the cannula 102. For example, the camera actuator 148 (e.g., providing two opposite push buttons 176), and the fluid port 150 can be part of the connection hub 108. In this case, the cannula 102, the imaging system 104, and the connection hub 108 together form a portion 116 of the endoscopic device 100 that can be used for a single-use operation to be disposed of following an examination of a patient's uterus. The portion 116 can be provided in a sealed, sterile package that can be stored until a time of use. The display 112 and the handle 114 together form a reusable portion 118 of the endoscopic device 100 that is designed to be attached to and detached from several single-use portions 116 to respectively examine multiple patients' uteruses. The reusable portion 118 is sterilized (e.g., cleaned and disinfected) following examination of each patient's uterus (e.g., prior to examining a next patient's uterus).

The cannula 102 typically has a total length (e.g., as measured along the primary axis 122) of about 30.0 cm to about 34.0 cm (e.g., about 32.0 cm). The proximal end region 110 of the cannula 102 (e.g., the portion of the cannula 102 that is disposed within the connection hub 108) typically has a length of about 4.0 cm to about 4.6 cm (e.g., about 4.3 cm), such that a remaining portion of the cannula 102 extends distally from the connection hub 108 and is therefore exposed for insertion into the patient. The distal bend 124 typically has a radius of about 2.5 cm to about 7.5 cm (e.g., about 5.0 cm). The shaft 120 typically has a wall thickness of about 0.03 cm to about 0.05 cm (e.g., about 0.04 cm) and an inner diameter (e.g., a luminal diameter) of about 0.34 cm to about 0.36 cm (e.g., about 0.35 cm).

The shaft 120 is typically made of one or more materials that are flexible enough to allow the cannula 102 to bend by a small amount to be appropriately placed within the patient as desired, yet stiff enough to permit easy insertion into the vaginal canal. Example materials from which the shaft 120 is typically made include nylon, polysulfone, and polyether ether ketone (PEEK). The cannula 102 is typically manufactured primarily via extrusion and via secondary processes that may include one or more of punching, laser cutting, forming, and/or printing. The coupler 126 is typically made of one or more materials including liquid crystal polymer (LCP) and is typically secured to the distal end 106 of the shaft 120 via adhesive.

The housing 146 is generally axially aligned with the primary axis 122 of the cannula 102 and has a generally curved profile that is laterally symmetric. The housing 146 defines a distal opening 162 through which the cannula 102 passes, an opening 154 (e.g., aligned with the sidewall opening 144 of the shaft 120) to which the fluid port 150 is secured, an operative channel 164 that surrounds the operative conduit 156, the proximal opening 158, and an upper connection port 160 (e.g., a micro HDMI port or another type of port) to which the display 112 or a display cable can be connected. In this regard, the connection hub 108 also includes electrical components (e.g., a small PCB or a flex circuit with an EEPROM, not shown) that communicate the camera actuator 148 with the connection port 160. The housing 146 further defines additional internal wall features (e.g., flanges, openings, brackets, tabs, etc.) that properly position the fluid port 150, the camera actuator 148, the connection port 160, and the entry port 152.

The housing 146 of the connection hub 108 typically has a length (e.g., as measured along the primary axis 122 of the cannula 102) of about 10 cm to about 20 cm (e.g., about 15 cm) and a maximum width of about 20 cm to about 30 cm (e.g., about 25 cm). The housing 146 typically has a handle seating width (e.g., as defined by a distance between opposite surfaces of the receptacles 170) of about 1.4 cm to about 1.8 cm (e.g., about 1.6 cm). The housing 146 is typically made of one or more materials including acrylonitrile butadiene styrene (ABS) or polycarbonate or copolyester and is typically manufactured via injection molding.

The operative channel 164 can include an operative conduit 156 that may be curved or straight. The operative conduit is typically made of one or more materials including polyvinyl chloride (PVC). In some embodiments, the curved profile of the operative conduit 156 provides space needed within the connection hub 108 for one or more electronic components, such as a PCB. The operative conduit 156 is sized to allow passage of a working tool from the entry port 152 to the distal end 106 of the cannula 102.

The entry port 152 includes a valve assembly that is configured to receive a working tool without leakage of fluids or tissues from the entry port 152. Valve components of the entry port 152 are typically made of silicon or a thermoplastic elastomer. A rear location of the entry port 152 (e.g., at the proximal opening 158) facilitates insertion of a working tool into the endoscopic device 100, as compared to placement of a port along a top or side surface, as is typically the case with conventional devices.

The push buttons 176 of the camera actuator 148 serve as Snap/Video buttons that control capture (e.g., recording and/or storing) of still images and video from the camera 142, such that pressing either or both of the push buttons 176 for a threshold period (e.g., 1 second) or less results in capture of a single, still photo, whereas pressing either or both of the push buttons 176 for longer than the threshold period results in capture of a video recording. While a video is being recorded, a single press of a push button 176 stops capturing of the video. The push buttons 176 can be easily pressed with one or more of a user's fingers on the hand that is holding or inserting the endoscopic device 100. An overhanging edge 178 of the coupler 126 acts as a lens hood that shields light from directly impinging on the LEDs 138 and from entering an aperture of the camera 142.

The camera 142 includes a complementary metal-oxide-semiconductor (CMOS) sensor module, a lens, and a glass cover. The CMOS sensor module includes a low voltage color CMOS image sensor core, an image sensor processor, and an image output interface circuitry. By providing integrated digital video processing within the CMOS sensor module, some aspects of video processing can be performed directly on the same printed circuit board (PCB) as the CMOS sensor module, or on the same substrate in which the CMOS is formed such that the imaging plane of the CMOS and the plane along which the video processing circuits extend substantially coincide. Furthermore, the display 112 includes an image signal processing (ISP) chip that can perform additional aspects of the image processing and that can support various video formats. The video signal from the CMOS sensor module can be in any suitable video format, such as National Television System Committee (NTSC), Phase Alternating Line (PAL), or another common video format.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

A number of implementations have been described. Nevertheless, it will be understood that various modifications may be made without departing from the spirit and scope of the disclosure. For example, various forms of the flows shown above may be used, with steps re-ordered, added, or removed. The endoscopic devices described herein can be used in examining any body organs that is reachable through a body cavity. Accordingly, other implementations are within the scope of the following claims.

What is claimed is:

1. An endoscopic device, comprising:
   a housing;
   a cannula configured to be inserted through a cervix into a uterus, the cannula having a lumen that extends from a proximal end of the cannula to a distal end of the cannula, the proximal end of the cannula being secured within the housing, wherein the lumen is configured to provide a passage for a working tool;
   an imaging system arranged at the distal end of the cannula, the imaging system comprising:
   a camera, and
   one or more light-emitting diodes (LEDs) configured to provide light for the camera to acquire images of the uterus; and
   a flexible printed circuit (FPC) that extends within the lumen of the cannula and electrically connects the camera and the one or more LEDs to electrical components located in the housing;
   a tip element that holds the camera at the distal end of the cannula, wherein the tip element is designed to move through the cervix in a forward direction, and has a forward facing surface that faces the forward direction, the forward facing surface having at least one opening that exposes the camera at the distal end of the cannula; and
   a guiding element placed inside the cannula and proximate the tip element, the guiding element having a cavity that forms a channel configured for passing the working tool, wherein at least a portion of the guiding element has a ramp-shaped profile formed by a thickness difference between a distal thickness of the portion that is proximate the tip element and a proximal thickness of the portion that is farther away from the tip element than the distal thickness, wherein the thickness difference between the distal thickness and the proximal thickness causes the ramp-shaped profile to guide the working tool away from electrical contacts of the camera to the FPC.

2. The device of claim 1, wherein the cannula defines a proximal opening and a distal opening, the proximal and the distal openings being configured to allow a working instrument to enter the lumen via the proximal opening and exit the lumen via the distal opening.

3. The device of claim 1, wherein the electrical components in the housing includes at least one of a printed circuit board (PCB), a display, a display cable, and an electrical connection port.

4. The device of claim 1, wherein the FPC is shaped to conform with an inner surface of the lumen.

5. The device of claim 1, wherein the FPC is positioned within an upper third portion of the lumen.

6. The device of claim 1, wherein the working tool has a size of 5 French or smaller.

7. The device of claim 1, wherein the tip element holds the one or more LEDs at the distal end of the cannula, and wherein the tip element is configured to:
   allow a sensor of the camera to sense reflected LED lights, and
   block other light from entering the sensor of the camera.

8. The device of claim 7, wherein the tip element includes a partitioning wall that separates the camera from the one or more LEDs.

9. The device of claim 8, wherein the partitioning wall extends from a lens of the camera to a proximal end of the camera where the camera connects to the FPC.

10. The device of claim 7, wherein the tip element has a convex shape projecting outward from the distal end of the cannula.

11. The device of claim 7, wherein the tip element forms at least a portion of a tool channel configured to guide the working tool to exit the endoscopic device.

12. The device of claim 11, wherein the tool channel has a curved inner surface that projects outward towards the camera.

13. The device of claim 1, wherein the tip element holds the one or more LEDs at the distal end of the cannula, and wherein the device further comprises a coupler located between the tip element and a shaft that forms the lumen, the coupler having a coupler notch that fits into a notch of a distal tip of the shaft to prevent the coupler from rotating relative to the distal tip.

14. The device of claim 13, wherein the coupler has a thread formed by a bulge in an inner surface of the coupler, the thread being arranged at about a location where the coupler meets the distal tip of the shaft.

15. The device of claim 1, wherein a thickness of the portion of the guiding element increases from the proximal thickness to the distal thickness so that the guiding element protects the electrical contacts of the camera to the FPC from potential impacts caused by the working tool passing through the cannula towards the distal end of the cannula.

16. The device of claim 15, wherein the guiding element comprises a molded element that is positioned between the tip element and a distal end of a shaft of the cannula, wherein the shaft defines the lumen of the cannula.

17. The device of claim 16, further comprising a coupler element located between the distal end of the shaft and the tip element, the coupler element extending along the FPC and surrounding a distal portion of the FPC and the molded element.

18. The device of claim 17, wherein the molded element has an outer surface that includes one or more groves that receive one or more ribs of an inner surface of the coupler element.

19. The device of claim 17, wherein the coupler element has an inner surface that includes one or more grooves configured to receive one or more ribs of an outer surface of the molded element.

20. The device of claim 17, wherein the molded element has an inner surface that drafts down in diameter as the molded element extends towards the tip element.

21. The device of claim 17, wherein the coupler element has an inner surface that drafts down in diameter as the coupler extends towards the tip element.

22. The device of claim 17, wherein the guiding element has a surface compatible with a surface of at least one of the tip element or the coupler.

23. The device of claim 1, wherein the cannula is a double-lumen cannula comprising a first lumen and a second lumen, both the first and the second lumen extending along the cannula and being separated by a wall.

24. The device of claim 23, wherein the FPC passes through the first lumen, and the lumen that is configured to provide the passage for the working tool is the second lumen.

25. The device of claim 1, wherein the guiding element is secured to a surface of the FPC.

26. The device of claim 1, wherein the guiding element further comprises multiple extensions protruding from the guiding element and extending along a shaft of the cannula, the multiple extensions being configured to prevent the guiding element from rotating inside the cannula.

27. The device of claim 1, wherein the guiding element has an inclining lower surface that extends along a shaft of the cannula.

* * * * *